United States Patent
Myers

(10) Patent No.: US 6,290,682 B1
(45) Date of Patent: *Sep. 18, 2001

(54) INFUSION SET

(75) Inventor: Jan Willem Marinus Myers, Venlo (NL)

(73) Assignee: Filterek Inc., Hebron, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 09/079,062

(22) Filed: May 14, 1998

Related U.S. Application Data

(63) Continuation-in-part of application No. 08/800,779, filed on Feb. 13, 1997, now Pat. No. 5,935,100.

(30) Foreign Application Priority Data

May 14, 1997 (DE) .............................................. 197 20 054

(51) Int. Cl.⁷ ..................................................... A61M 5/00
(52) U.S. Cl. .......................................... 604/247; 604/256
(58) Field of Search ......................... 604/30, 33, 89–91, 604/80, 246, 247, 249, 283, 256, 258, 905; 251/149, 149.1; 137/843, 846, 850, 859, 516.17, 516.13

(56) References Cited

U.S. PATENT DOCUMENTS

| | | |
|---|---|---|
| 2,758,609 | 8/1956 | Dickert et al. . |
| 3,084,707 | 4/1963 | Frye . |
| 3,270,771 | 9/1966 | Morgan et al. . |
| 3,599,657 | 8/1971 | Maldavs . |
| 3,633,605 | 1/1972 | Smith . |
| 3,779,274 | 12/1973 | Kelly . |
| 4,089,349 | 5/1978 | Schenk . |
| 4,141,379 | 2/1979 | Manske . |
| 4,237,880 | 12/1980 | Genese . |
| 4,241,756 | 12/1980 | Bennett et al. . |
| 4,343,305 | 8/1982 | Bron . |
| 4,415,003 | 11/1983 | Paradis et al. . |
| 4,534,764 | 8/1985 | Mittleman et al. . |
| 4,556,086 | 12/1985 | Raines . |
| 4,593,720 | 6/1986 | Bergandy . |
| 4,646,781 | 3/1987 | McIntyre . |
| 4,712,583 | 12/1987 | Pelmulder et al. . |
| 4,729,401 | * 3/1988 | Raines .................................. 137/512 |
| 4,749,003 | 6/1988 | Leason . |
| 4,768,547 | 9/1988 | Danby et al. . |
| 4,846,215 | 7/1989 | Barree . |
| 4,958,661 | 9/1990 | Holtermann et al. . |
| 4,966,199 | 10/1990 | Ruschke . |
| 5,025,829 | 6/1991 | Edwards et al. . |
| 5,176,658 | * 1/1993 | Ranford ............................... 604/247 |
| 5,215,538 | 6/1993 | Larkin . |

(List continued on next page.)

FOREIGN PATENT DOCUMENTS

| | | |
|---|---|---|
| 667 675 | 4/1934 | (DE) . |
| GM 1 695 553 | 3/1953 | (DE) . |
| 1 675 370 | 2/1954 | (DE) . |

(List continued on next page.)

*Primary Examiner*—Richard K. Seidel
*Assistant Examiner*—Michael Hayes
(74) *Attorney, Agent, or Firm*—Brinks Hofer Gilson & Lione

(57) ABSTRACT

In an infusion set having a container for fluid medicines, which by a feed-line and a differential pressure valve is connected to a drip chamber and which by a further feed-line is connected to a front end controlled with a roller clamp according to U.S. patent application Ser. No. 08/800,779, the differential pressure valve has two inlets each with an associated differential force chamber and the two differential force chambers are sealingly separated from each other by a diaphragm disk, wherein both differential force chambers are connected to an exit line for the fluid medicine. To use the differential pressure valve, the valve is configured as a 3-way check valve by the fact that the first inlet is connected to the container for the fluid medicine and that the second inlet is designed for the connection to a syringe or the like.

20 Claims, 5 Drawing Sheets

U.S. PATENT DOCUMENTS

| | | | |
|---|---|---|---|
| 5,267,964 | * 12/1993 | Karg | 604/141 |
| 5,453,097 | 9/1995 | Paradis . | |
| 5,520,661 | 5/1996 | Lal et al. . | |
| 5,617,897 | 4/1997 | Myers . | |
| 5,771,935 | 6/1998 | Myers . | |
| 5,935,100 | 8/1999 | Myers . | |

FOREIGN PATENT DOCUMENTS

| | | |
|---|---|---|
| 27 13 618 C2 | 10/1977 | (DE) . |
| 30 35 301 A1 | 4/1981 | (DE) . |
| 8214927.5 | 5/1982 | (DE) . |
| 82 14 927.5 | 9/1982 | (DE) . |
| 32 15 329 A1 | 12/1982 | (DE) . |
| 86 03 917 U1 | 5/1986 | (DE) . |
| 38 03 380 | 8/1989 | (DE) . |
| 40 39 814 A1 | 6/1992 | (DE) . |
| 92 09 491.0 | 10/1992 | (DE) . |
| 41 42 494 A1 | 7/1993 | (DE) . |
| 42 01 258 A1 | 7/1993 | (DE) . |
| 93 19 810.8 U1 | 3/1994 | (DE) . |
| 43 09 262 A1 | 6/1994 | (DE) . |
| 43 04 949 A1 | 8/1994 | (DE) . |
| GM 93 10 673.4 | 9/1994 | (DE) . |
| 196 05 217 | 2/1996 | (DE) . |
| GM 296 10 419.1 | 12/1996 | (DE) . |
| 195 45 421 A1 | 6/1997 | (DE) . |
| 0 072 800 B1 | 3/1983 | (EP) . |
| 0 562 246 A1 | 9/1993 | (EP) . |
| 0 612 537 A2/A3 | 8/1994 | (EP) . |
| 2 666 745 A | 3/1992 | (FR) . |
| 2 027 168 A | 2/1980 | (GB) . |
| WO 88/02639 | 4/1988 | (WO) . |
| WO88/02639 | 4/1988 | (WO) . |
| WO 89/02764 | 4/1989 | (WO) . |
| WO 91/11641 | 8/1991 | (WO) . |
| WO 96/03166 | 2/1996 | (WO) . |
| WO 97/47339 | 12/1997 | (WO) . |

* cited by examiner

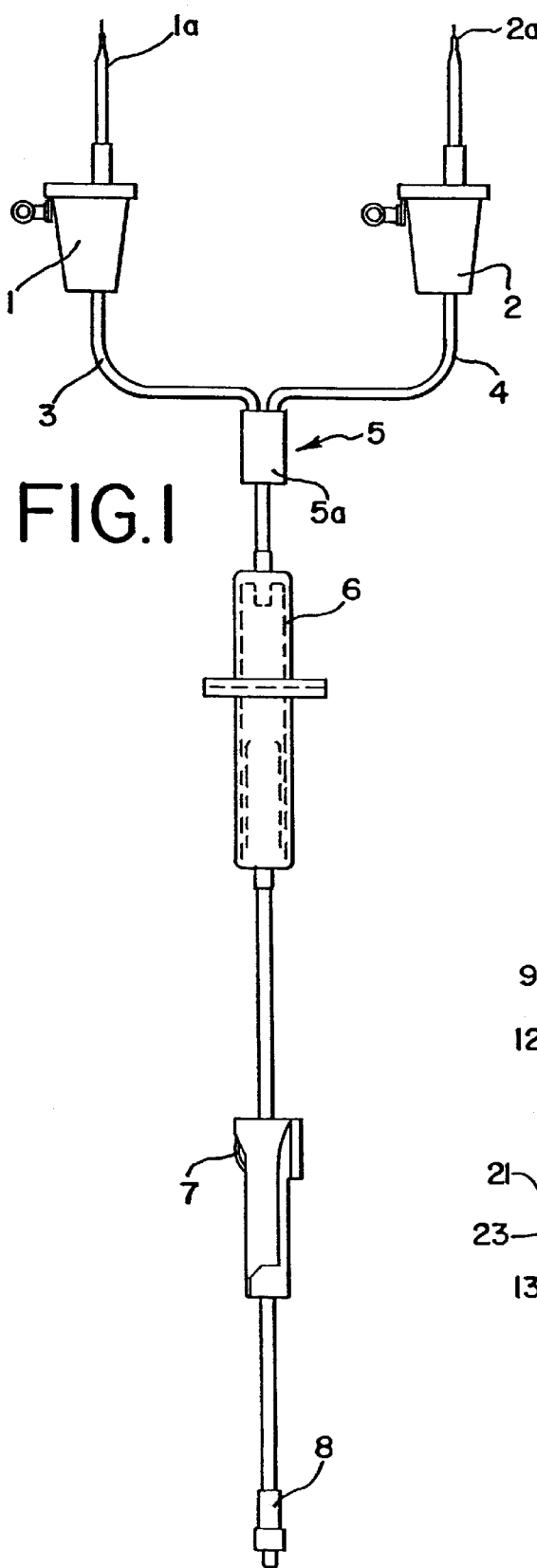
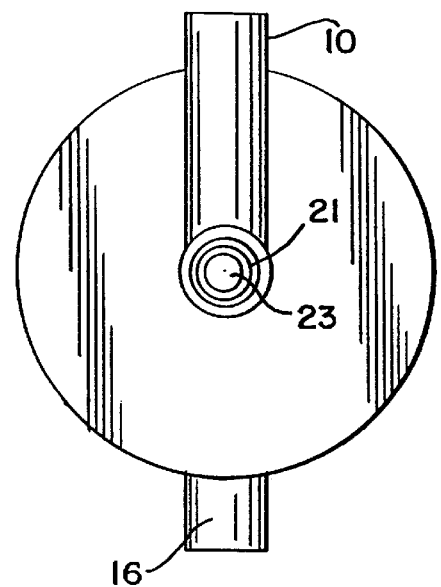
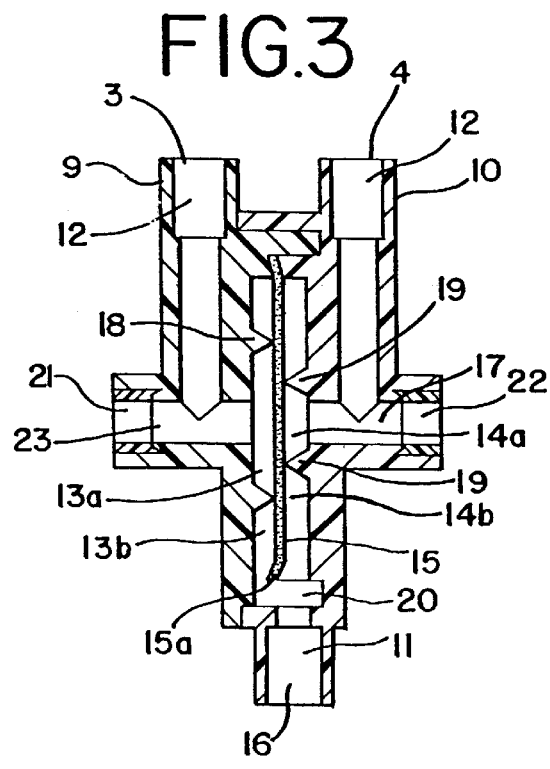

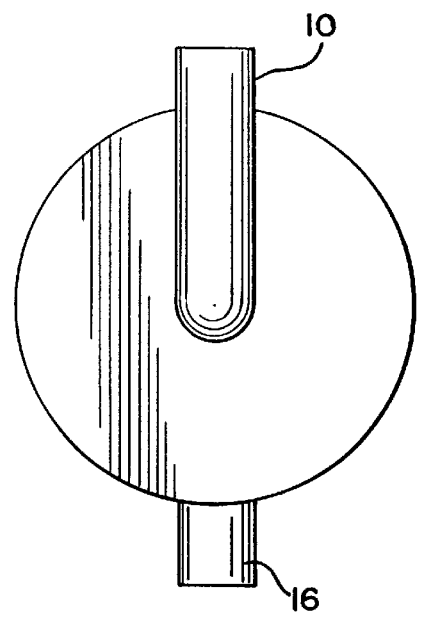
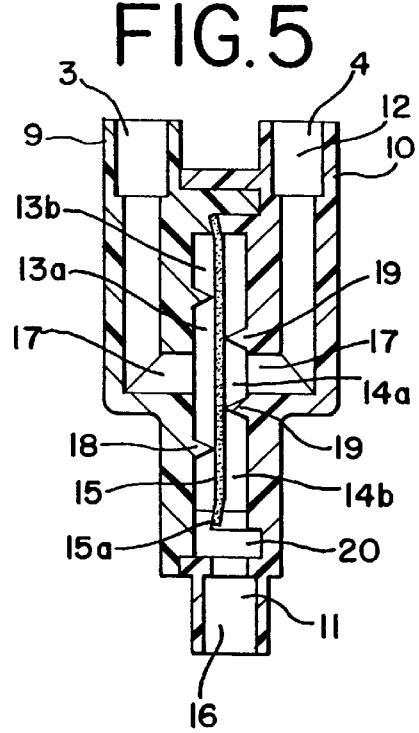
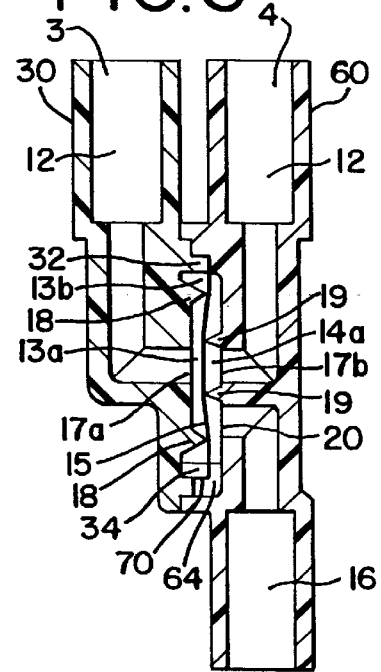
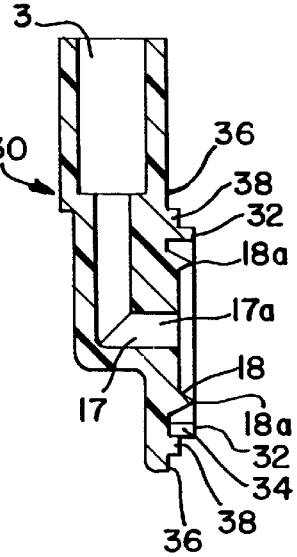
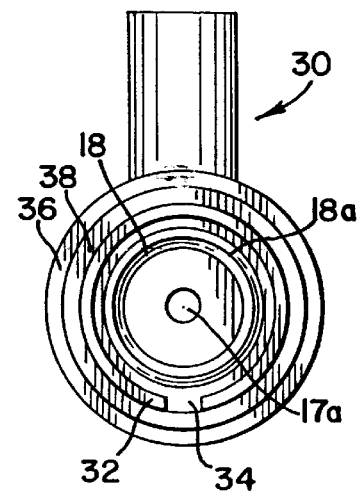

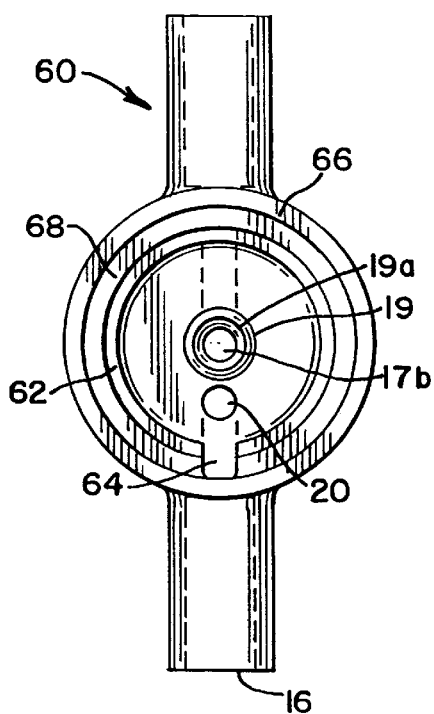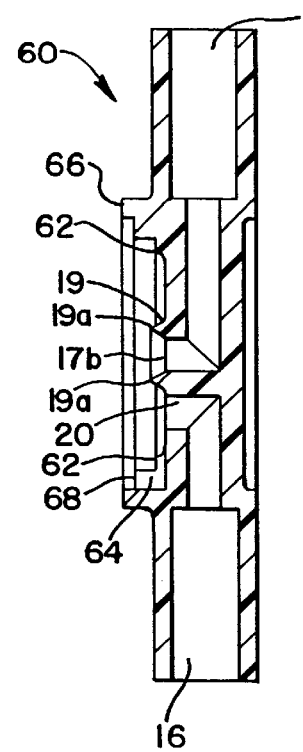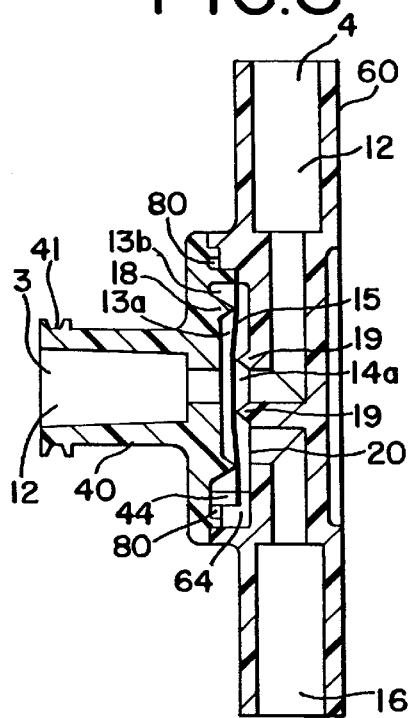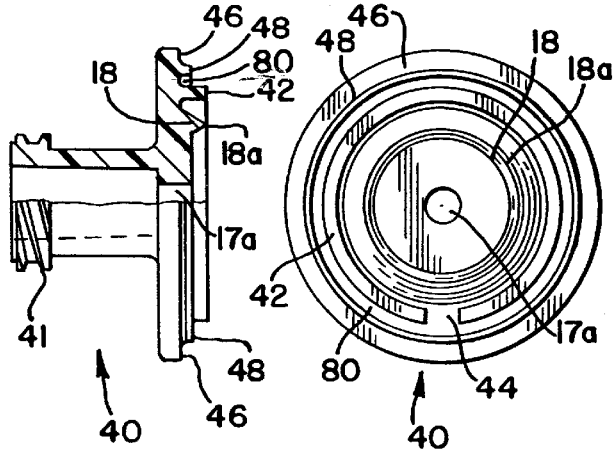

INFUSION SET

This application is a continuation in part of U.S. application Ser. No. 08/800,779, filed Feb. 13, 1997, now issued as U.S. Pat. No. 5,935,100.

BACKGROUND OF THE INVENTION

The invention relates to an infusion set having a container for liquid medicines, which is connected to a drip chamber by a feed-line and a differential pressure valve and by a further feed-line connected to a front end being controlled by a roller clamp. A similar structure is disclosed in U.S. patent application Ser. No. 08/800,779, now issued as U.S. Pat. No. 5,935,100, which is hereby incorporated by reference. In the disclosed structure, the differential pressure valve has two inlets, each with an associated differential force chamber, wherein the two differential force chambers are sealingly separated from each other by a diaphragm disk and, wherein further the two differential force chambers together are connected to an exit line for the liquid medicine.

In the infusion set according to U.S. patent application Ser. No. 08/800,779, the differential pressure valve is performed such that it is used to empty sequentially a number of containers filled with liquid medicines in a controlled way.

In known infusion sets, an additional check valve is necessary to prevent a contamination of the set in the case of an occlusion or the like. Further, in many cases, it is necessary while the infusion is going on to administer additional amounts in a surge-like manner or to additionally inject, for example, contrast substances.

SUMMARY OF THE INVENTION

In an infusion set of the present invention, this aim is achieved by the fact that the differential pressure valve is configured as a 3-way check valve by the first inlet being connected to the container for the liquid medicine and by the second inlet being configured for the connection to a syringe or the like.

In an preferred embodiment according to the invention, the first inlet is provided with a male "Luer-Lock"-connector and the second inlet has a female "Luer-Lock"-connector.

According to a preferred embodiment of the invention, the valve comprises two valve housing halves sealingly connectable with each other, wherein one valve housing half has the first inlet and the second valve housing half has the exit line and the second inlet. In detail, it is of advantage that the two valve housing halves are connectable with each other. Within the differential force chambers each valve housing has an annular ridge concentric to a liquid inlet or liquid outlet, respectively, wherein the first inlet which is connected to the container is associated with an annular ridge having a larger diameter and the outlet line is associated with an annular ridge having a smaller diameter.

It is further preferred in this connection that the diaphragm disk is positioned with a part of its circumference at an opening which leads to the second inlet.

A further improvement of the invention consists of the fact that the liquid outlet of the exit line coaxially opening to the annular ridge having the larger diameter has an angular shape and that the liquid inlet of the first inlet opening is coaxial to the other annular ridge and extends coaxially to the first inlet.

The desired valve action with an excellent sealing at very small pressures is achieved by the fact that the diaphragm disk has a circular shape and is manufactured from a sheet of liquid silicone, silicone or natural rubber or a strip of liquid silicone, silicone or natural rubber.

The invention is described in more detail with reference to the drawings.

BRIEF DESCRIPTION OF THE DRAWINGS

As set forth, in part, in U.S. Pat. No. 5,935,100:

FIG. 1 is a general side view of an embodiment of the assembled components for an infusion set.

FIG. 2 is a side view of an embodiment of a differential pressure valve with air relief lines.

FIG. 3 is a central axial cross-section of the differential pressure valve of FIG. 2.

FIG. 4 is a side view of an alternative embodiment of a differential pressure valve without air relief lines.

FIG. 5 is a central axial cross-section of the differential pressure valve of FIG. 4.

FIG. 6 is a central axial cross-section of another embodiment of a differential pressure valve that has a side view similar to that of FIG. 4.

FIG. 6a is a central axial cross-section of a component of the differential pressure valve of FIG. 6.

FIG. 6b is a plan view of the differential pressure valve component of FIG. 6a.

FIG. 7a is a central axial cross-section of a second component of the differential pressure valve of FIG. 6.

FIG. 7b is a plan view of the differential pressure valve component of FIG. 7a.

FIG. 8 is a central axial cross-section of another embodiment of the differential pressure valve that has a different first component than FIG. 6.

FIG. 8a is partially broken-out central axial cross-section of a first component of the differential pressure valve of FIG. 8.

FIG. 8b is a plan view of the differential pressure valve component of FIG. 8a.

DETAILED DESCRIPTION OF THE DRAWINGS AND PREFERRED EMBODIMENTS OF THE INVENTION

Figure 9:
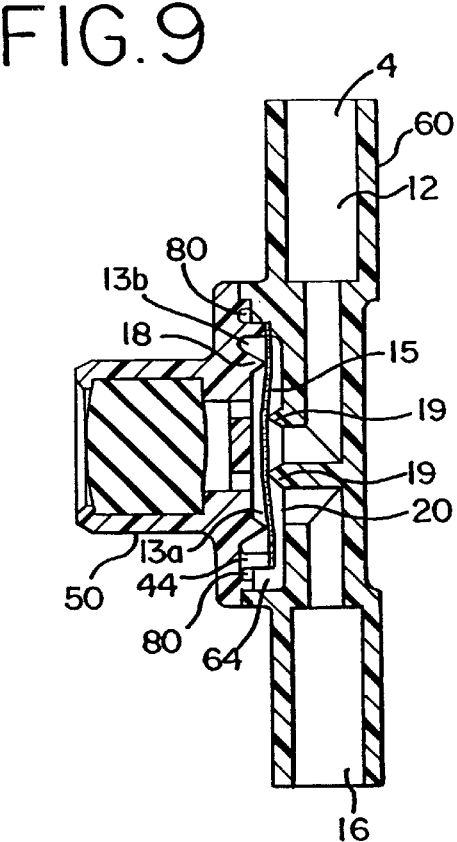
FIG. 9 is a central axial cross-section of yet another embodiment of the differential pressure valve that has another first component than FIG. 6.
Figure 10:
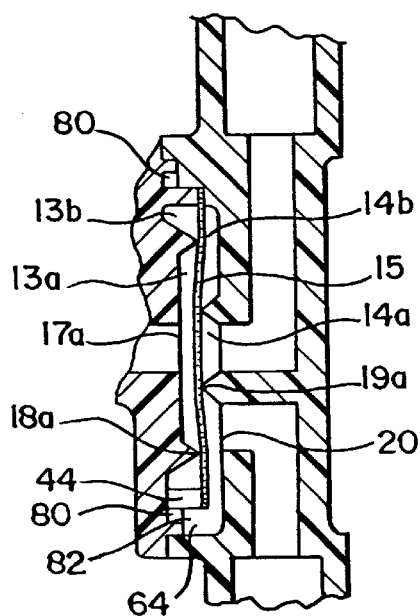
FIG. 10 is a magnified partially broken out central axial cross-section of the embodiment of the differential pressure valve of FIG. 8.

In the drawings, the further constituents of the infusion set, namely, the container for the liquid medicines, the lines, the drip chamber, the roller clamp and so on are briefly discussed here. Since these constituents are known and since the differential pressure valve forms the core of the present invention.

As set forth, in part, in U.S. Pat. No. 5,935,100:

As shown in FIG. 1, a first container 1 is used for a chosen liquid medicine which can be different from the liquid medicine in a second container 2 or which can be the same. The liquid medicine is introduced by piercing means such as spikes 1a or 2a, respectively, that are for example from an ampulla. The first container 1 is connected to a first feed line 3 and the second container 2 is connected to a feed line 4 and both feed lines are connected to a valve 5 consisting of a differential pressure valve 5a more detailedly described below. The fluid medicine communicates with a drip chamber 6 via valve 5 and associated line and is under the control of a roller clamp 7 that in turn is fed to the front end 8 of the infusion set from where as usual it is introduced into the body of a patient.

With reference to FIGS. 4–5, the differential pressure valve comprises two valve housing halves 9 and 10 which are adapted to sealingly contact each other, and after the mounting of the diaphragm disk 15 therein, the valve housing halves 9 and 10 are sealed together thereby clamping securely diaphragm disk 15 therebetween. One of the valve housing halves, either half 9 or half 10, includes a drain line entry 11 for connection to an appropriate drain line 16, and each valve housing half 9 and 10 also includes a feed line entry 12. Valve housing halves 9 and 10 when assembled together with diaphragm disk 15 provide differential force chambers 13 and 14, respectively, within the valve. Annular ridge 18 of housing half 9 may, depending upon operating conditions as discussed below, establish a seal with diaphragm disk 15 that demarcates differential force chamber 13 into a circular chamber 13a and annular chamber 13b. Similarly, annular ridge 19 of housing half 10 may, again depending upon the operating conditions more fully explained below, establish a seal with diaphragm disk 15 that demarcates differential force chamber 14 into a circular chamber 14a and annular chamber 14b. Accordingly, the respective annular ridges 18, 19 may also be termed lip-shaped sealing rings 18, 19. Annular ridge 18 has a larger diameter than annular ridge 19.

Diaphragm disk 15 includes a perimeter portion 15a positioned at opening 20 that leads to the drain line 16. In this embodiment, diaphragm disk 15 is circular and produced from a sheet of liquid silicone, silicone rubber, or natural rubber or from a mat of liquid silicone, silicone rubber or natural rubber, and thus portion 15a is a part of the circumference of diaphragm disk 15. Further, opening 20 is in direct fluid communication with annular chamber 13b and annular chamber 14b irrespective of whether diaphragm disk 15 is sealed against annular ridges 18, 19. Also, in direct fluid communication with circular chambers 13a, 14a are fluid channels 17. In this embodiment, fluid channels 17 open coaxially to the respective circular chambers 13a, 14a and annular ridges 18, 19, and provide a fluid path that is at an angled shape, such as a 90° elbow.

The diaphragm disk 15 is preferably circular and stamped or die cut from a sheet or band of liquid silicone, silicone rubber, or natural rubber. The thickness of the diaphragm is preferably uniform and may vary, dependent on the desired pressure differential between chambers, from 0.2 to 0.5 mm. The thickness tolerance varies by the manufacturing method of the sheet or mat of the diaphragm material. The preferred embodiment consists of silicone rubber and has a diameter of about 13.5 mm, a thickness of about 0.3 mm, and a hardness of 40 degrees Shore A.

An alternative embodiment is shown in FIGS. 6–7b, in which like reference numerals indicate like parts and features as the above figures. Primary housing half 60 and secondary housing half 30 are sealingly engaged. Like the other embodiments, one housing half includes annular ridge 18 provided with a sealing lip apex 18a and the other housing half is provided with annular ridge 19 that includes sealing lip apex 19a. Secondary housing 30 (see FIGS. 6a–6b) is provided with inlet 17a, about which is located annular ridge 18. Secondary housing 30 includes a compression ring 32 that projects from the secondary housing 30 body and has a diameter greater than annular ridge 18. Compression ring 32 is provided with compression ring passage 34, that in conjunction with valve space passage 64 (discussed below) allows for fluid communication between annular chambers 13b and 14b in the assembly of the housing halves 30, 60. Secondary housing 30 is further provided with first sealing ring projection 36 that has a diameter greater than that of the compression ring 32 and allows for sealing engagement of the housing halves. Secondary housing 30 may also have a secondary sealing ring 38 that may provide an alternative sealing engagement member for the assembly.

Primary housing half 60 (see FIGS. 7a–7b) is provided with inlet 17b about which is located annular ridge 19, that in turn includes sealing lip apex 19a. Outside of annular ridge 19 is located opening 20 that is in fluid communication with drain line 16 (see FIGS. 7a–7b). Encircling annular ridge 19 and opening 20 is ring shaped seat 62 that is discontinuous and provided with a valve space passage 64. Ring shaped seat 62 is adapted to clamp diaphragm disk 15 between ring shaped seat 62 and compression ring 32 when the housing halves are assembled (see FIG. 6). Encircling ring shaped seat 62 is sealing ring projection 66 which is continuous and adapted to engage first sealing ring projection 36 of the secondary housing when the housing halves are assembled. Intermediate sealing ring projection 66 and ring shaped seat 62 is secondary sealing ring 68 that is of sufficient height to allow for the fluid communication between compression ring passage 34 and valve space passage 64 when the housing halves are assembled. The aforementioned combination of the valve space passage 64 overlying compression ring passage 34 provides a bypass channel 70 in the assembled housing halves (see FIG. 6). This bypass channel 70 is generally radial in configuration in this embodiment, and the overlying radial passages 34 and 64 are assured in the assembly by way of orienting the respective feed line entry 12 passage in a parallel condition.

In the assembly of the housing halves, the housing halves are sealed together at the interface between the first sealing ring projection 36 and sealing ring projection 66, which in turn clamps the diaphragm 15 between ring shaped seat 62 and compression ring 32. Such joinder may be executed by means of ultrasonic welding or use of medically approved adhesives (e.g., ultraviolet curing adhesives), or a combination thereof The presently preferred sealing means employs ultrasonic welding. The clamped interface between the disk 15, ring shaped seat 62 and compression ring 32 may also be executed by means of ultrasonic welding or use of medically approved adhesives.

An alternative secondary housing half 40 is shown in FIGS. 8a–8b, that in turn may be assembled with primary housing half 60. This assembly is shown in FIG. 8. Referring now in more detail to these drawings, in which like reference numerals indicate like parts and features throughout the several of the above-discussed views, secondary housing 40 (see FIGS. 8a–8b) is generally provided with a threaded connection 41 for connecting the housing half 40 to an appropriate liquid medicine feedline. With this design, there is thus the possibility to connect the housing half by means of a male luerlock connection or other medically accepted threaded connection.

Further, alternative secondary housing 40 includes a compression ring 42 that projects from the housing 40 that is a diameter greater than annular ridge 18. Secondary housing 40 is further provided with sealing ring projection 46, of a diameter greater than compression ring 42 that permits sealing engagement between housing halves, and secondary sealing ring 48 may provide an alternative sealing engagement for the assembly. Compression ring passage 44, in this embodiment, is generally radial and allows for fluid communication between the annular chamber 13b and annular channel 80 provided in secondary housing 40.

In the preferred embodiments of the differential pressure valves, the valve housings may be manufactured of polymeric materials that are generally medically accepted, e.g. polystyrenes, styrenic copolymers (A.B.S.) or polycarbonates. In particular, the preferred material is a styrenic copolymer (A.B.S.) manufactured by BASF Corporation, and sold under the trademark name of Teriux KR2802.

Figure 11:
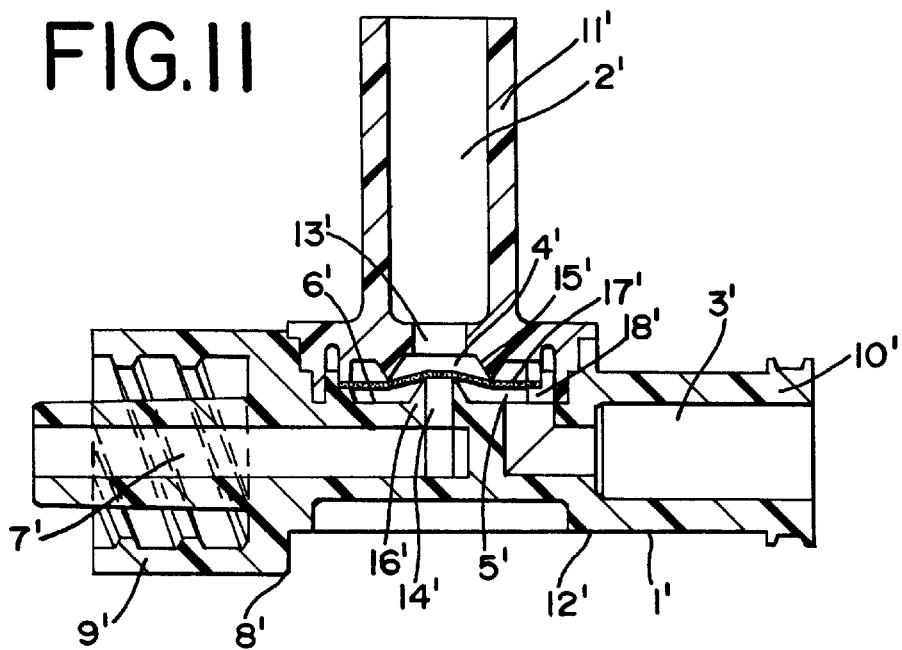
FIG. 11 is a cross-sectional view of the differential pressure valve in its embodiment as a 3-way check valve.

As especially can be seen in FIG. 11, the preferred differential pressure valve 1' has two inlets 2' and 3', which are each open to a differential pressure chamber 4' or 5', respectively. The two differential pressure chambers 4' and 5' are sealingly separated from each other by a diaphragm disk 6'. Both differential pressure chamber 4' and 5' together are in communication with an exit line 7' for the liquid medicine, wherein the exit line 7' is usually connected to the line leading to a drip chamber, while the first inlet is usually connected to the flask or container of the liquid medicine by means of a suitable line.

The differential pressure valve 1' according to FIG. 11 is configured as a 3-way check valve 8' when the first inlet 2' is connected to the container for the liquid medicine (not shown) and when the second inlet 3' is designed for the connection to a syringe or the like (not shown).

Figure 12:
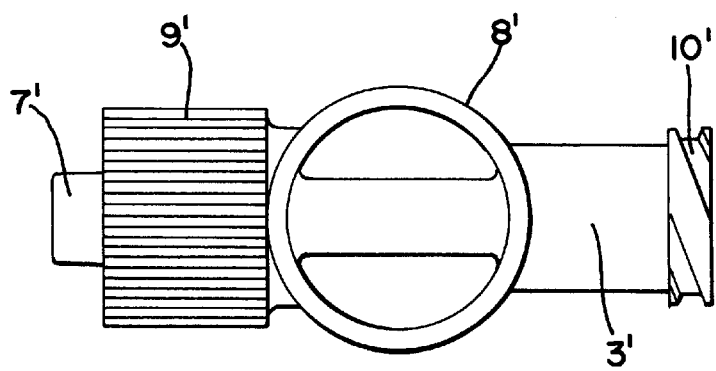
FIG. 12 is a bottom view of the valve of FIG. 1.
Figure 13:
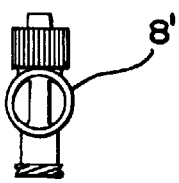
FIG. 13 is an embodiment of the valve in its actual size.

As shown in FIGS. 11–13, the exit line 7 has a male "Luer-Lock"-connector 9' and the second inlet 3 has a female "Luer-Lock"-connector 10, wherein the sizes are chosen such that by means of the slight tapering of the second inlet 3, the front end of a typical syringe can be received in a form-fit manner.

The housing of the differential pressure valve 1' is made of two valve housing halves 11' and 12', which are sealingly connectable with each other. The valve housing half 11' contains the first inlet 2' and the second valve housing half 12' contains the second inlet 3' and the exit line 7'. The valve housing half 11' has an annular ridge 15' within the differential force chamber 4', the ridge 15' being concentric to a liquid inlet 13'. The valve housing half 12' has an annular ridge 16' within the differential force chamber 5', concentric to a liquid outlet 14'. The sizes of ridges 16' and 15' are such that the annular ridge 15' has a larger diameter, and is associated with the first inlet 2', which is connected to the container for the liquid medicine. The annular ridge 16', having a smaller diameter, is associated with the exit line 7 leading to the drip chamber.

The diaphragm disk 6 is positioned between the two housing halves 11 and 12' with a part 17' of its circumference lying at an opening 18 leading to the second inlet 3. The liquid outlet 14 of the exit line 7 has an angular shape and is coaxial to the annular ridge 16 as shown in FIG. 1. The liquid inlet 13 of the inlet 2 is coaxial to the annular ridge 15, which is also coaxial to the inlet 2.

The circular diaphragm disk 6 is manufactured from a sheet of liquid silicone, silicone or natural rubber or a strip of silicone, liquid silicone, silicone or natural rubber.

The operation of the 3-way check valve 8 is such that during a normal infusion, the infusion liquid is guided from the inlet 2', to the outlet line 7'. If liquid medicine is drawn from the container of the liquid medicine by means of a syringe at the inlet 3', the diaphragm 6 is pressed against the annular ridge 16 because of the vacuum created on the bottom side, which means that liquid is not drawn from the line 7 leading to the patient. If, on the other hand, additional liquid or possibly a different medicine is injected at the second inlet 3, then because of the correspondingly created pressure, the diaphragm disk 6 is pressed against the upper annular ridge 15, which means that the additional liquid is guided exclusively via the exit line 7 from the second inlet 3 to the patient, and cannot reach the line leading back to the container connected to the first inlet 2.

The preferred embodiment of the invention thus provides an extremely compact 3-way check valve which consists merely of three parts, namely, the first valve housing half 11', the second valve housing half 12', and the diaphragm 6' positioned therebetween.

As set forth, in part, in U.S. Pat. No. 5,935,100:

The disclosed valve is of simple construction, yet provides a reliable valve for operating pressures to which it is suited. It is believed that with the construction of this pressure differential valve as disclosed, the tension in the diaphragm disk can be accurately predetermined and provide automatic switching between fluid sources at predetermined hydrostatic pressures. In this manner, the present invention avoids complicated designs and yet may result in reliably achieving the above-noted pressure differential valve functionality. Further, the design of the above-described embodiments avoids complicated assembly methods by way of limiting the number of highly tolerated dimensions or assembly methods and the like and thus they lend themselves to assemblage by automated equipment.

It should be appreciated that the apparatus of the present invention is capable of being incorporated in the form of a variety of embodiments, only one of which has been illustrated and described above. The invention may be embodied in other forms without departing from its spirit or essential characteristics. The described embodiment is to be considered in all respects only as illustrative and not restrictive, and the scope of the invention is, therefore, indicated by the appended claims rather than by the foregoing description. All changes which come within the meaning and range of equivalency of the claims are to be embraced within their scope.

I claim:

1. An infusion set having a container for liquid medicine, which is connected to a drip chamber by a feed-line and a differential pressure valve, the dip chamber connected by a further feed-line to a front end with a roller clamp, and a syringe connected to a differential pressure valve, characterized in that the differential pressure valve having a housing, a diaphragm disk retained about the perimeter thereof by the housing, a first inlet associated with an outlet annular ridge and in fluid communication with the diaphragm disk, and a second inlet in fluid communication with the diaphragm and the outlet annular ridge and the first inlet annular ridge, wherein the differential pressure valve is configured as a 3-way check valve by the first inlet being connected to the container for the liquid medicine and the second inlet being configured for the connection to the syringe whereby under normal valve operation is not sealingly engaging the first inlet annular ridge and the outlet annular ridge such that the first inlet is in fluid communication with the outlet, and when pressure is created by the syringe between the first inlet annular ridge and the outlet annular ridge the diaphragm sealingly engages in the first inlet annular ridge, and when negative pressure is created by the syringe between the first inlet annular ridge and the outer annular ridge the diaphragm sealingly engages the outlet annular ridge.

2. The infusion set according to claim 1, further characterized in that the outlet comprises a male "Luer-Lock"-connector or the second inlet comprises a female "Luer-Lock"-connector.

3. The infusion set according to claim 1, further characterized in that the differential pressure valve comprises a first housing half and a second valve housing half connected with each other with the diaphragm disk therebetween, wherein the first valve housing half comprises the first inlet and the second valve housing half comprises the outlet and the second inlet.

4. The infusion set according to claim 3, further characterized in that the first valve housing half comprises the first inlet annular ridge with the first inlet annular ridge concentric to the first inlet, and the second valve housing half comprises the outlet annular ridge, with the outlet annular ridge being concentric to the outlet, and wherein the first inlet, which is connected to the container, is associated with an annular ridge having a first diameter, and wherein the outlet is associated with an annular ridge having a smaller diameter than said first diameter.

5. The infusion set according to claim 3, further characterized in that the diaphragm disk is positioned between the first valve housing half and the second valve housing half, with a part of the diaphragm disk circumference at an opening leading to the second inlet.

6. The infusion set according to claim 4, further characterized in that the outlet annular ridge is oriented coaxially to the first inlet annular ridge.

7. The infusion set according to claim 1, further characterized in that the diaphragm disk has a circular shape and is produced from a liquid silicone, silicone or natural rubber sheet or a liquid silicone, silicone or natural rubber strip.

8. The infusion set according to claim 7, further characterized in that the outlet annular ridge has a diameter, and the first inlet annular ridge has a diameter and wherein the outlet annular ridge diameter is smaller than the first inlet annular ridge diameter.

9. The infusion set according to claim 8, further characterized in that the outlet annular ridge is coaxial with the first inlet annular ridge.

10. The infusion set according to claim 9, further characterized in that the differential pressure valve comprises a first valve housing half and a second valve housing half sealed together with the diaphragm disk therebetween.

11. The infusion set according to claim 10, wherein the first valve housing half comprises the first inlet and the second valve housing half comprises the outlet and the second inlet.

12. The infusion set according to claim 11, wherein the outlet comprises a male luer lock connector or the second inlet comprises a female luer lock connector.

13. A three way check valve adapted for connection to a container for liquid medicine, a syringe, and an outlet line, comprising a housing, a diaphragm disk retained about the perimeter thereof by the housing, a first inlet associated with a first inlet annular ridge and in fluid communication with the container for liquid medicine and the diaphragm disk, an outlet associated with an outlet annular ridge and in fluid communication with the outlet line and the diaphragm disk, and a second inlet in fluid communication with the syringe and the diaphragm and the outlet annular ridge and the first inlet annular ridge, whereby under normal valve operation the diaphragm is not sealingly engaging the first inlet annular ridge and the outlet annular ridge such that the first inlet is in fluid communication with the outlet, and when pressure is created by the syringe at the second inlet and between the first inlet annular ridge and the outlet annular ridge, the diaphragm sealingly engages the first inlet annular ridge, and when negative pressure is created by the syringe between the first inlet annular ridge and the outlet annular ridge the diaphragm sealingly engages the outlet annular ridge.

14. The three way check valve of claim 13, wherein the outlet annular ridge diameter is smaller than the first inlet annular ridge diameter.

15. Three way check valve of claim 14, further characterized in that the outlet annular ridge is coaxial with the first inlet annular ridge.

16. Three way check valve of claim 15, wherein the diaphragm disk is produced from a liquid silicone, silicone or natural rubber sheet or a liquid silicone, silicone or natural rubber strip.

17. Three way check valve of claim 16, further characterized in that the three way check valve comprises a first valve housing half and a second valve housing half sealed together with the diaphragm disk therebetween.

18. Three way check valve of claim 17, wherein the first valve housing half comprises the first inlet and the second valve housing half comprises the outlet and the second inlet.

19. Three way check valve of claim 18, wherein the outlet comprises a male luer lock connector or the second inlet comprises a female luer lock connector.

20. Three way check valve of claim 19, wherein the diaphragm disk is positioned within the housing such that a portion of its circumference is located at an opening leading to the second inlet.

* * * * *

UNITED STATES PATENT AND TRADEMARK OFFICE
CERTIFICATE OF CORRECTION

PATENT NO. : 6,290,682 B1
DATED : September 18, 2001
INVENTOR(S) : Jan William M. Myers It is certified that error appears in the above-identified patent and that said Letters Patent is hereby corrected as shown below:

Column 6,
Line 45, delete "dip" and substitute -- drip -- in its place;
Line 50, after "with" insert -- a first inlet annular ridge and in fluid communication with the diaphragm disk, an outlet associated with --;
Line 58, delete "operation is not" and substitute -- operation the diaphragm is not -- in its place;
Line 63, delete "in";
Line 65, delete "outer" and substitute -- outlet -- in its place.

Column 7,
Line 6, after "first" insert -- valve --.

Signed and Sealed this

Fifth Day of November, 2002

Attest:

Attesting Officer

JAMES E. ROGAN
Director of the United States Patent and Trademark Office